(12) United States Patent
Abe

(10) Patent No.: US 10,357,397 B2
(45) Date of Patent: Jul. 23, 2019

(54) LASER TREATMENT APPARATUS

(71) Applicant: NIDEK CO., LTD., Gamagori, Aichi (JP)

(72) Inventor: Hitoshi Abe, Okazaki (JP)

(73) Assignee: NIDEK CO., LTD., Gamagori, Aichi (JP)

(*) Notice: Subject to any disclaimer, the term of this patent is extended or adjusted under 35 U.S.C. 154(b) by 975 days.

(21) Appl. No.: 14/264,424

(22) Filed: Apr. 29, 2014

(65) Prior Publication Data

US 2014/0324031 A1 Oct. 30, 2014

(30) Foreign Application Priority Data

Apr. 30, 2013 (JP) ................... 2013-094876

(51) Int. Cl.
*A61F 9/008* (2006.01)

(52) U.S. Cl.
CPC .... *A61F 9/008* (2013.01); *A61F 2009/00863* (2013.01); *A61F 2009/00868* (2013.01); *A61F 2009/00897* (2013.01)

(58) Field of Classification Search
CPC .................................................... A61F 9/008
USPC ................... 606/2–19; 607/86–94
See application file for complete search history.

(56) References Cited

U.S. PATENT DOCUMENTS

| 6,010,497 A | 1/2000 | Tang et al. |
| 6,132,424 A * | 10/2000 | Tang .................. A61F 9/008 606/10 |

| 2004/0111083 A1 | 6/2004 | Gross et al. |
| 2004/0243111 A1 | 12/2004 | Bendett et al. |
| 2004/0243112 A1 | 12/2004 | Bendett et al. |
| 2005/0102008 A1 | 5/2005 | Wong |
| 2008/0147052 A1 | 6/2008 | Bendett et al. |

(Continued)

FOREIGN PATENT DOCUMENTS

| JP | 2005-527317 A | 9/2005 |
| JP | 2011-156290 A | 8/2011 |
| JP | 2012-120858 A | 6/2012 |

OTHER PUBLICATIONS

Kishiko Ohkoshi, "Subthreshold and Micropulse Diode Laser Photocoagulation for Macular Disease", Journal of Ophthalmic Surgery, published Jul. 30, 2007, pp. 365-369, vol. 20, No. 3.

(Continued)

*Primary Examiner* — Carl H Layno
*Assistant Examiner* — Dacheng Xie
(74) *Attorney, Agent, or Firm* — Sughrue Mion, PLLC

(57) ABSTRACT

A laser treatment apparatus configured to emit laser light onto a tissue of a patient's eye, the laser treatment apparatus includes: a laser scanner configured to scan laser light emitted from a laser light source and switch a position of the tissue onto which laser light is emitted; a processor; and memory storing computer readable instructions, which are executed by the processor, causing the laser treatment apparatus to: (a) emit the laser light onto a first spot; (b) stop emitting the laser light onto the first spot for a stop time; (c) emit the laser light onto at least one second spot other than the first spot during the stop time; (d) emit the laser light onto the first spot again after the stop time elapses; and repeat (b), (c) and (d) several times to execute intermittent irradiation treatment onto a plurality of spots multiple times.

17 Claims, 8 Drawing Sheets

(56) References Cited

U.S. PATENT DOCUMENTS

| | | | |
|---|---|---|---|
| 2009/0075816 A1* | 3/2009 | Kawahara | B41J 2/471 503/201 |
| 2011/0245816 A1* | 10/2011 | Abe | A61F 9/00821 606/4 |
| 2012/0013915 A1* | 1/2012 | Okamura | A61B 3/102 356/479 |
| 2012/0215208 A1 | 8/2012 | Bendett et al. | |
| 2017/0020733 A1 | 1/2017 | Bendett et al. | |

OTHER PUBLICATIONS

Communication dated Feb. 21, 2018, issued by the Japanese Patent Office in counterpart Japanese application No. 2014-085536.

* cited by examiner

FIG. 4
< LINEAR PATTERN >
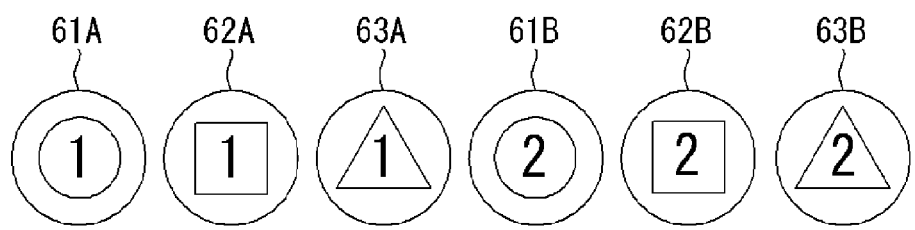
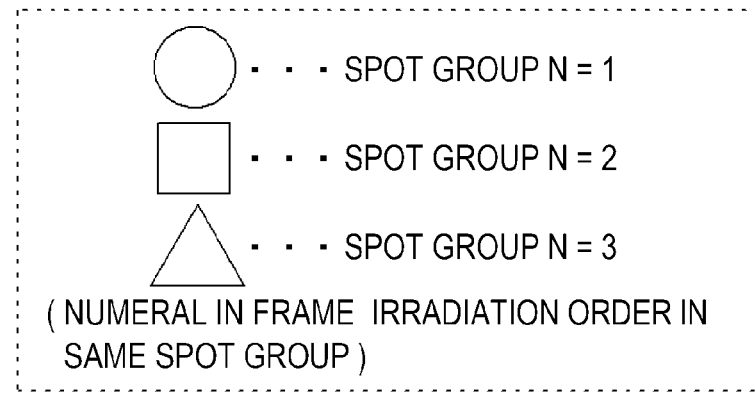

TRIANGULAR PATTERN

LASER TREATMENT APPARATUS

CROSS REFERENCE TO RELATED APPLICATION

This application is based upon and claims the benefit of priority of Japanese Patent Application No. 2013-094876 filed on Apr. 30, 2013, the contents of which are incorporated herein by reference in its entirety.

BACKGROUND

The present disclosure relates to a laser treatment apparatus which emits laser light onto the tissue (for example, fundus, trabecular, or the like) of a patient's eye to treat the tissue.

In the related art, a technique (hereinafter, referred to as "intermittent irradiation treatment") in which laser light is intermittently emitted onto one place in the tissue of a patient's eye multiple times to treat the tissue is known. For example, Non-Patent Document 1 discloses a treatment technique for retinal pigment epithelium by micro-pulse as a typical example of the intermittent irradiation treatment technique. In the treatment technique disclosed in "OHKO-SHI Kishiko, "Subthreshold and Micropulse Diode Laser Photocoagulation for Macular Disease", Journal of Ophthalmic Surgery 20: 365-369, 2007", irradiation of laser light in a very short time is performed for one spot intermittently multiple times with a stop time. If intermittent irradiation of laser light for one spot ends, intermittent irradiation for another spot is performed.

SUMMARY

When laser light is intermittently emitted onto one place multiple times to perform treatment, it is necessary to provide a stop time between the respective laser irradiations. Accordingly, in the intermittent irradiation treatment of the related art, it is not easy to reduce the time necessary for treatment.

The present disclosure provides a laser treatment apparatus capable of reducing a treatment time when laser light is intermittently emitted onto each place multiple times to treat the patient's eye.

According to the laser treatment apparatus of the present disclosure, it is possible to reduce treatment time when laser light is intermittently emitted onto each place multiple times to treat the patient's eye.

An aspect of the present invention provides the following arrangements:

A laser treatment apparatus configured to emit laser light onto a tissue of a patient's eye, the laser treatment apparatus comprising:

a laser scanner configured to scan laser light emitted from a laser light source and switch a position of the tissue onto which laser light is emitted;

a processor; and memory storing computer readable instructions, which are executed by the processor, causing the laser treatment apparatus to:

(a) emit the laser light onto a first spot;

(b) stop emitting the laser light onto the first spot for a stop time;

(c) emit the laser light onto at least one second spot other than the first step during the stop time;

(d) emit the laser light onto the first spot again after the stop time elapses; and repeat (b), (c) and (d) several times to execute intermittent irradiation treatment onto a plurality of spots multiple times.

A method of controlling a laser treatment apparatus configured to emit laser light onto a tissue of a patient's eye, the laser treatment apparatus including a laser scanner configured to scan laser light emitted from a laser light source and switch a position of the tissue onto which laser light is emitted, the method comprising:

(a) emitting the laser light onto a first spot;

(b) stopping emitting the laser light onto the first spot for a stop time;

(c) emitting the laser light onto at least one second spot other than the first step during the stop time;

(d) emitting the laser light onto the first spot again after the stop time elapses; and repeating (b), (c) and (d) several times to execute intermittent irradiation treatment onto a plurality of spots multiple times.

BRIEF DESCRIPTION OF THE DRAWINGS

FIG. 4 is a diagram showing an example of the arrangement and spot groups of a linear pattern.

DESCRIPTION OF EXEMPLARY EMBODIMENTS

Figure 1:
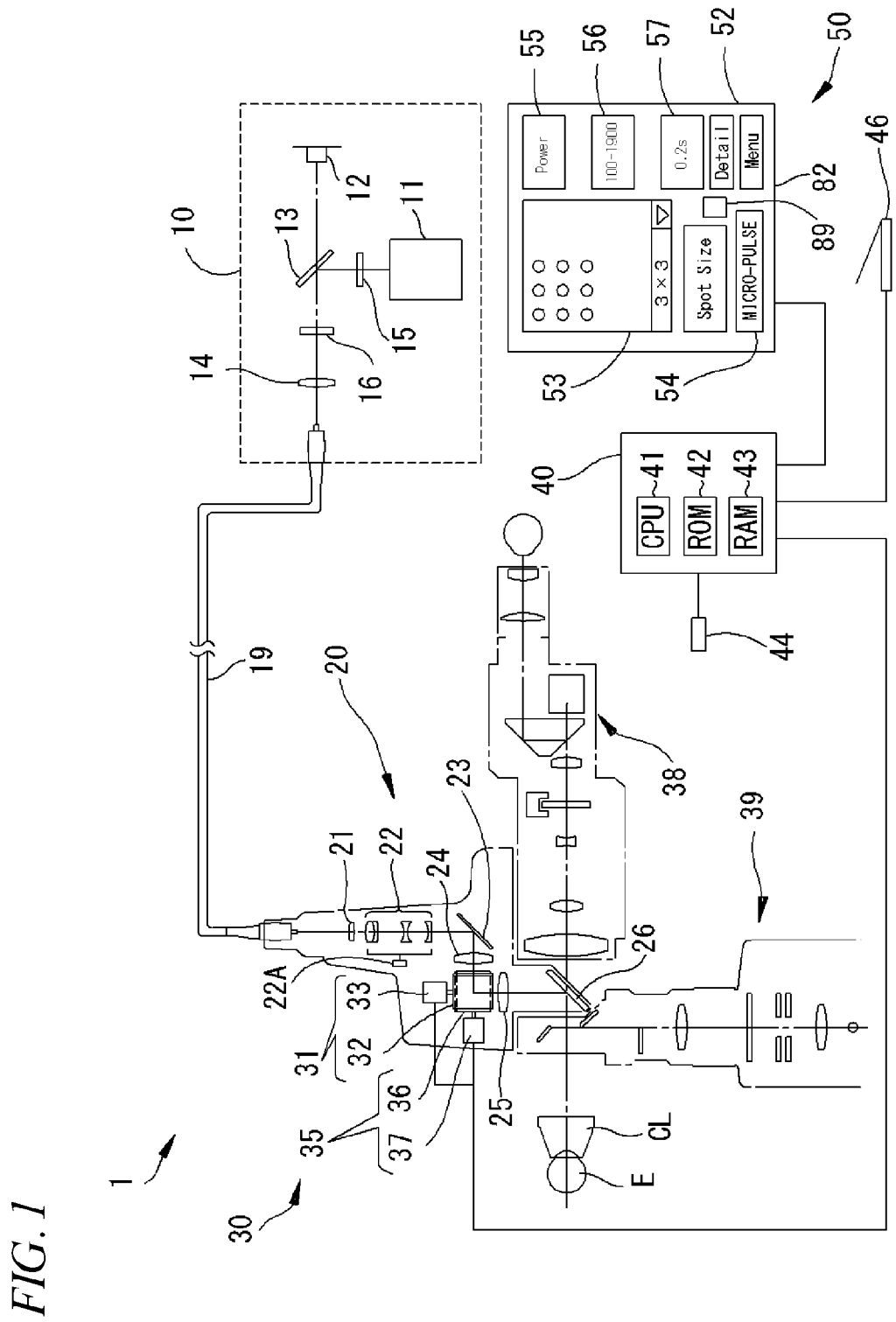
FIG. 1 is a diagram showing the schematic configuration of a laser treatment apparatus 1.

Hereinafter, an embodiment of the present disclosure will be described referring to the drawings. First, the schematic configuration of a laser treatment apparatus 1 according to the present embodiment will be described referring to FIG. 1. The laser treatment apparatus 1 according to the present embodiment includes a laser light source unit 10, a laser irradiation optical system 20, an observation optical system 38, an illumination optical system 39, a controller 40, and an operating unit 50.

<Laser Light Source Unit>

The laser light source unit 10 includes a laser light source 11, an aiming light source 12, a beam splitter 13, a condensing lens 14, a first shutter 15, and a second shutter 16.

The laser light source 11 emits treatment laser light for treating the tissue of a patient's eye E. The aiming light source 12 emits aiming light which indicates the position of a treatment spot (that is, a position where treatment laser light is emitted). In this embodiment, a light source which emits visible laser light is used as the aiming light source 12. An operator inputs an instruction to emit treatment laser light to the laser treatment apparatus 1 in a state where aiming light is aimed at a region to be treated, causing treatment laser light to be emitted onto a desired region of the patient's eye E.

The beam splitter 13 multiplexes treatment laser light and aiming light. The beam splitter 13 according to the present embodiment reflects a majority of treatment laser light and transmits a part of aiming light, thereby multiplexing treatment laser light and aiming light. The condensing lens 14 condenses laser light incident from the beam splitter 13 and causes laser light to be incident on an incident end surface of an optical fiber 19. The laser treatment apparatus 1 may emit treatment laser light and aiming light onto the patient's eye E from separate optical paths without multiplexing treatment laser light and aiming light. In this case, the laser treatment apparatus 1 does not need to include a configuration for multiplexing treatment laser light and aiming light.

The first shutter 15 and the second shutter 16 block the optical paths at abnormality, thereby increasing safety for the patient, the operator, and the like. The first shutter 15 is provided in an optical path between the laser light source 11 and the beam splitter 13. The second shutter 16 is provided in an optical path along which both treatment laser light and aiming light are guided.

The laser light source unit 10 alternately repeats the on/off of emission of treatment laser light, thereby emitting treatment laser light in a pulse form. As an example, in this embodiment, an excitation source of the laser light source 11 which is SHG (Second Harmonic Generation) laser is controlled by the controller 40 such that pulsed treatment laser light is emitted from the laser light source 11. However, a method of emitting pulsed treatment laser may be changed. For example, the laser treatment apparatus 1 may turn continuous-wave laser (CW) emitted from the laser light source 11 to a pulse form by a device (for example, the first shutter 15 or the second shutter 16) provided outside the laser light source 11. For a gain medium of the laser light source 11, for example, known mediums, such as Nd:YAG, Nd:YVO$_4$, Nd:YLF, Ho:YAG, Er:YAG, Yb:YAG, and Yb:YVO$_4$, may be used.

Though details are not shown, a plurality of laser light sources 11 may be detachably mounted in the laser light source unit 10 according to the present embodiment. For example, in the laser light source unit 10, a laser light source 11 which emits treatment laser light having a wavelength of 577 nm and a laser light source 11 which emits treatment laser light having a wavelength of 532 nm may be mounted at the same time. When a plurality of laser light sources 11 are mounted in the laser light source unit 10, the operator can operate the operating unit 50 described below to select the laser light source 11 (that is, the wavelength of the treatment laser light) for use in treatment. Accordingly, the operator can select appropriate treatment laser light among a plurality of kinds of treatment laser light without changing a device for use in treatment. The operator may add, change, or the like the laser light source 11 as necessary.

<Laser Irradiation Optical System>

The laser irradiation optical system 20 emits laser light (in this embodiment, treatment laser light and aiming light incident through the optical fiber 19) incident from the laser light source unit 10 onto the tissue (for example, fundus, trabecular, or the like) of the patient's eye E. The laser irradiation optical system 20 according to the present embodiment is a delivery mounted in a slit lamp (not shown). The laser irradiation optical system 20 includes a relay lens 21, a zoom lens 22, a mirror 23, a collimator lens 24, a laser scanner 30, an objective lens 25, and a reflecting mirror 26.

The zoom lens 22 moves the optical axis direction of laser light so as to change the spot size of laser light incident from the relay lens 21. The position of the zoom lens 22 is detected by an encoder 22A. The controller 40 described below detects the spot size of laser light to be emitted onto the tissue on the basis of the position of the zoom lens 22 detected by the encoder 22A. A configuration for changing the spot size of laser light may be changed. For example, the laser treatment apparatus 1 may include a plurality of lenses having different magnifications, and may switch a lens to be inserted into the optical axis of laser light to change the spot size.

Laser light passing through the zoom lens 22 is incident on the laser scanner 30 through the mirror 23 and the collimator lens 24. The laser scanner 30 scans laser light, thereby moving the irradiation position of laser light in the tissue. Laser light passing through the laser scanner 30 passes through the objective lens 25, is reflected by the reflecting mirror 26, and is emitted onto the tissue of the patient's eye E through a contact lens CL.

Figure 2:
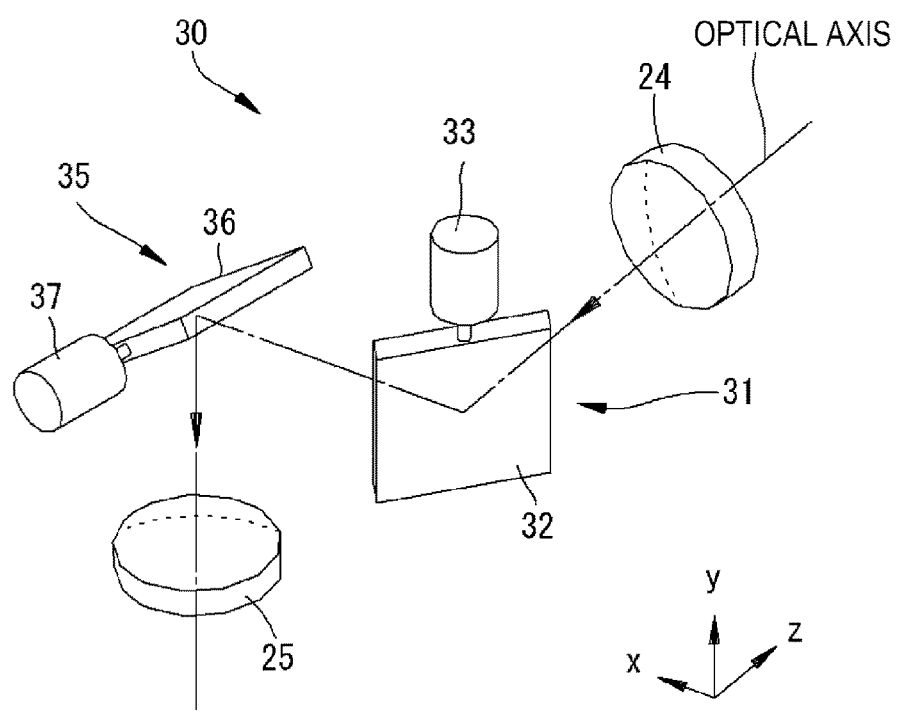
FIG. 2 is a perspective view of a laser scanner 30.

The laser scanner 30 will be described. As shown in FIG. 2, the laser scanner according to the present embodiment includes a first galvanomirror (galvanoscanner) 31 and a second galvanomirror 35. The first galvanomirror 31 includes a mirror 32 and an actuator 33. The oscillation axis of the mirror 32 extends in a y-axis direction, and the mirror 32 scans laser light in an x direction. The second galvanomirror 35 includes a mirror 36 and an actuator 37. The oscillation axis of the mirror 36 extends in a z-axis direction, and the mirror 36 scans laser light in the y direction. The actuators 33 and 37 are embedded with a motor and a potentiometer. The controller 40 described below separately oscillates (rotates) the two mirrors 32 and 36 on the basis of positional information detected by the potentiometers. As a result, laser light is scanned in a two-dimensional manner.

The laser treatment apparatus which scans laser light on the fundus of the patient's eye should scan laser light in a given range. For example, if a scanning range is narrow, it is difficult to emit laser light in a wide arrangement pattern, such as a 5×5 arrangement pattern described below.

In order to emit laser light in a given range, it is necessary to set the size of a reflective surface of at least one of the galvanomirrors 31 and 35 to be equal to or greater than a given size. For example, it is preferable that, of the two galvanomirrors 31 and 35, the reflective surface of the galvanomirror 35 on the downstream side of the optical path has a size equal to or greater than 8 mm in the axial direction of the oscillation axis. More preferably, the size of the reflective surface of the galvanomirror 35 in the axial direction of the oscillation axis is equal to or greater than 10 mm. In this embodiment, the galvanomirrors 31 and 35 have a size in which a length in the axial direction of the oscillation axis is 12 mm and a width in a direction orthogonal to the oscillation axis is 7 mm.

In order to emit laser light in a given range, it is necessary to set a rotatable angle of at least one of the galvanomirrors 31 and 35 to be equal to or greater than a given angle. For example, at least one of the two galvanomirrors 31 and 35 can rotate at equal to or greater than ±1.5 degrees around an origin position. More preferably, at least one of the galvanomirrors 31 and 35 can rotate at equal to or greater than ±2.0 degrees around the origin position. In this embodiment, each of the two galvanomirrors 31 and 35 can rotate at equal to or greater than ±3.0 degrees.

The laser scanner 30 according to the present embodiment scans laser light using the two galvanomirrors 31 and 35. Accordingly, the laser scanner 30 according to the present embodiment can scan laser light on the fundus in a wide range compared to a different scanner is used. However, a specific configuration of the laser scanner 30 may be changed. For example, a polygon mirror, a MEMS scanner, or the like may be used for the laser scanner 30. A device (for example, an acoustooptical element (AOM) or the like) which deflects laser light, instead of using the mirror reflection or the like, may be used for the laser scanner 30. The laser scanner 30 according to the present embodiment scans both treatment laser light and aiming light. However, a scanner which scans treatment laser light and a scanner which scans aiming light may be separately provided.

<Observation Optical System/Illumination Optical System>

The observation optical system 38 is used when the operator observes the patient's eye E. The observation optical system 38 according to the present embodiment includes an objective lens, a variable power optical system, a protective filter, an erect prism group, a field stop, an eyepiece lens, and the like. The illumination optical system 39 illuminates the patient's eye E. The illumination optical system 39 according to the present embodiment includes an illumination light source, a condenser lens, a slit, a projection lens, and the like, and illuminates the patient's eye E with slit light. In this embodiment, the observation optical system 38 and the illumination optical system 39 are mounted in the laser irradiation optical system 20 which is a slit lamp.

<Controller>

The controller 40 includes a CPU (processor) 41, a ROM 42, a RAM 43, a nonvolatile memory 44, and the like. The CPU 41 performs control of the respective units in the laser treatment apparatus 1. The ROM 42 stores various programs, initial values, and the like. The RAM 43 temporarily stores various kinds of information. The nonvolatile memory 44 is a non-fugitive storage medium which is able to hold the stored contents even if the supply of power is shut off. For example, a USB memory, a flash ROM, or the like which is detachably mounted in the controller 40 may be used as the nonvolatile memory 44.

To the controller 40 are connected the treatment laser light source 11, the aiming light source 12, the encoder 22A, the actuators 33 and 37, a foot switch 46, the operating unit 50, and the like. The foot switch 46 is stepped by the operator to input an instruction to start the irradiation of treatment laser light to the controller 40. A configuration for inputting the irradiation start instruction to the controller 40 may be changed. For example, a button which is operated by hand, a touch panel, or the like may be used as input means for inputting the irradiation start instruction.

<Operating Unit>

The operating unit 50 is operated by the operator so as to allow the operator to input various instructions to the laser treatment apparatus 1. In this embodiment, a touch panel-type display 52 is operated to input various instructions. However, it is needless to say that a keyboard, a mouse, a button, or the like may be used as the operating unit 50. The display screen of the display 52 shown in FIG. 1 is an example of a screen which is displayed during treatment. On the display screen shown in FIG. 1, an arrangement pattern setter 53, a treatment mode setter 54, an output setter 55, an intermittent irradiation pattern setter 56, an intermittent irradiation time setter 57, and the like are displayed.

The arrangement pattern setter 53 is operated so as to set the arrangement pattern of treatment laser light. The arrangement pattern is the pattern of arrangement of spots onto which treatment laser light is emitted each time the irradiation start instruction is input once. That is, the arrangement pattern represents the arrangement of spots to be treated by each irradiation start instruction on the tissue of the patient's eye. In the example shown in FIG. 1, an arrangement pattern (3×3 square pattern) for irradiating treatment laser light onto 9 spots in total of vertical 3 places×horizontal 3 places is shown. In this embodiment, for example, a pattern in which spots are arranged in a 2×2 square shape, a pattern in which spots are arranged in a 4×4 square shape, a pattern in which spots are arranged in a 5×5 square shape, a pattern in which spots are arranged in a curved shape, a fan-shaped pattern in which a plurality of arc-shaped arrangements are arranged in a radial direction, a pattern in which spots are arranged in a linear shape, and the like are prepared in advance. A single pattern having one spot may be prepared. In this embodiment, a user (operator or the like) may operate the operating unit 50 to create a desired arrangement pattern. The operator operates the arrangement pattern setter 53 to designate an arrangement pattern for use in treatment among one or a plurality of prepared arrangement patterns. The CPU 41 of the controller 40 sets the designated arrangement pattern as an arrangement pattern for use in treatment.

The treatment mode setter 54 is operated so as to set the mode of the laser treatment apparatus 1 when performing treatment. In this embodiment, as the treatment mode, a single irradiation mode and a micro-pulse irradiation mode (intermittent irradiation mode) are provided. The single irradiation mode is a mode in which treatment laser light having energy (power×pulse width) higher than energy in the micro-pulse irradiation mode is emitted onto each spot once. In this embodiment, treatment which is executed in the single irradiation mode is referred to as single irradiation treatment. The micro-pulse irradiation mode is a mode in which the pulse of treatment laser light having energy lower than energy in the single irradiation mode is emitted onto each spot intermittently multiple times at a pulse width of a microsecond order (for example, 25 microseconds to 10000 microseconds). Treatment in the micro-pulse irradiation mode is a kind of treatment (intermittent irradiation treatment) in which laser light is emitted on one place intermittently multiple times. The tissue of the patient's eye E is treated by micro-pulse, thereby suppressing diffusion of heat by treatment laser light from the region to be treated to the surroundings. As a result, adverse influence (for example, when treating retinal pigment epithelium, degradation of a macular function by heat diffusion, or the like) by heat diffusion is suppressed. In the single irradiation mode, treatment laser light (for example, continuous-wave (CW) treatment laser light having an irradiation time in an order of several hundreds of milliseconds) having high energy is emitted onto the tissue, whereby photocoagulation occurs in the tissue. For example, photocoagulation is used for prevention of proliferation of retinal neovascularity, treatment of retinal detachment, or the like. In this embodiment, the above-described arrangement pattern is used in both the single irradiation mode and the micro-pulse irradiation mode. That is, the term "single" in the single irradiation mode represents that treatment laser light is emitted onto one spot or each of a plurality of spots once in response to each irradiation instruction, instead of representing that treatment laser light is emitted once in response to each irradiation start instruction.

The laser treatment apparatus 1 according to the present embodiment switches the control method of the laser light source 11, thereby allowing both pulsed treatment laser in the micro-pulse irradiation mode and continuous-wave treatment laser in the single irradiation mode to be emitted from the same laser light source 11. However, a light source which emits pulsed treatment laser and a light source which emits continuous-wave treatment laser may be separately mounted in the laser light source unit 10. The laser treatment apparatus 1 according to the present embodiment scans both laser light for use in the intermittent irradiation treatment and laser light for use in the single irradiation treatment by the same laser scanner 30. Accordingly, the configuration of the laser scanner 30 is simplified.

The output setter 55 is operated so as to set the output of treatment laser light. The operator can set both the output in the single irradiation mode and the output in the micro-pulse irradiation mode by the output setter 55.

The intermittent irradiation pattern setter 56 is operated so as to set an intermittent irradiation pattern in the intermittent irradiation treatment (in this embodiment, treatment in the micro-pulse irradiation mode). The intermittent irradiation pattern is an irradiation mode when pulsed treatment laser light (hereinafter, simply referred to as "pulse") is emitted onto each spot multiple times. In detail, in this embodiment, parameters which are determined by the intermittent irradiation pattern include a pulse width, a stop time (see FIGS. 5 and 7), and an irradiation cycle time (see FIGS. 5 and 7). The pulse width is the on time (irradiation time) of each pulse which is emitted onto one spot multiple times. The stop time is the time from when the irradiation of the pulse onto one spot is stopped until the irradiation of the pulse onto the same spot starts. The irradiation cycle represents a serial cycle from when the irradiation of the pulse onto one spot starts until the irradiation of the pulse onto the same spot starts after the stop time. The irradiation cycle includes a single irradiation cycle in which a pulse is emitted onto one spot and a parallel irradiation cycle in which pulses are emitted onto a plurality of spots in parallel in the same irradiation cycle. If two of the three parameters of the pulse width, the stop time, and the irradiation cycle time are determined, the remaining parameter is automatically determined.

As an example, in this embodiment, an intermittent irradiation pattern having a pulse width of 100 microseconds and a stop time of 1900 microseconds, an intermittent irradiation pattern having a pulse width of 200 microseconds and a stop time of 1800 microseconds, and an intermittent irradiation pattern having a pulse width of 300 microseconds and a stop time of 1700 microseconds are provided in advance. A worker operates the intermittent irradiation pattern setter 56, thereby selecting one among the three intermittent irradiation patterns provided in advance. The laser treatment apparatus 1 according to the present embodiment executes the intermittent irradiation treatment according to the irradiation cycle (pulse width, stop time, and irradiation cycle time) selected (set) in advance before the irradiation of treatment laser light starts. In this embodiment, in all the three intermittent irradiation patterns provided in advance, the irradiation cycle time is set to 2000 microseconds (=2 milliseconds). In this case, the pulse of treatment laser light is emitted onto each spot intermittently multiple times at every 2000 microseconds. It is needless to say that the contents, number, and the like of the intermittent irradiation patterns provided in advance may be changed. The worker may operate the operating unit 50 to set the parameters of the intermittent irradiation patterns. In the micro-pulse treatment, it is preferable that an appropriate stop time for diffusing heat enough to prevent heat generated from a region to be emitted by each pulse from affecting other regions is set. For example, it is preferable that the stop time is set in a range of 75 microseconds to 10000 microseconds. It is preferable that the wavelength of treatment laser light is in a range of 520 nm to 615 nm.

The intermittent irradiation time setter 57 is operated so as to set the intermittent irradiation time. The intermittent irradiation time is the time necessary for intermittent irradiation treatment for one spot (see FIGS. 5 and 7). That is, the pulse of treatment laser light is emitted onto each spot multiple times for the intermittent irradiation time. Accordingly, when the intermittent irradiation time is 0.2 seconds and the irradiation cycle time is 2000 microseconds, the pulse is emitted onto each spot 100 times. The worker operates the intermittent irradiation time setter 57, thereby setting a desired intermittent irradiation time.

Micro-pulse irradiation processing which is executed by the laser treatment apparatus 1 according to the present embodiment and an irradiation mode of treatment laser light by the intermittent irradiation treatment according to the present embodiment will be described referring to FIGS. 3 to 9. The micro-pulse irradiation processing is executed by the CPU 41 of the controller 40 when the micro-pulse irradiation mode is set by the treatment mode setter 54. The CPU 41 executes the micro-pulse irradiation processing shown in FIG. 3 according to a control program stored in the ROM 42 or the nonvolatile memory 44.

First, it is determined whether or not an arrangement pattern is designated (S1). As described above, the operator operates the arrangement pattern setter (see FIG. 1), thereby designate an arrangement pattern. If an arrangement pattern is not designated (S1: NO), it is determined whether or not the irradiation start instruction is performed (S4). In this embodiment, the operator operates the foot switch 46 (see FIG. 1) to input the irradiation start instruction. If the irradiation start instruction is not input (S4: NO), the process returns to the determination of S1.

If an arrangement pattern is designated (S1: YES), the designated arrangement pattern is set (for example, stored in the RAM 43) as an arrangement pattern for use in treatment (S2). Next, the CPU 41 drives the laser scanner 30 (see FIG. 2) while turning on the aiming light source 12, thereby allowing aiming light to be emitted onto the tissue of the patient's eye E in the set arrangement pattern (S3). Aiming light is continuously emitted until the timing at which irradiation ends (for example, the timing at which an instruction to end treatment is input) is reached. The process progresses to determination of S4.

An irradiation mode of aiming light will be described. In this embodiment, if the irradiation start instruction of treatment laser light is input, treatment laser light is emitted onto one or a plurality of spots onto which aiming light is emitted. That is, aiming light is sequentially emitted onto the respective spots in the arrangement pattern. Accordingly, the operator can easily recognize a spot, on which treatment laser light is emitted, by aiming light. In this embodiment, not only before the irradiation start instruction of treatment laser light is performed but also while the irradiation start instruction is performed and treatment laser light is emitted onto the tissue, aiming light is emitted according to the arrangement pattern. Therefore, as in the micro-pulse irradiation treatment, when the intermittent irradiation treatment in which a treatment trace by a treatment laser action is difficult to visually recognize is performed, the operator easily recognizes the position where treatment laser light is emitted.

The irradiation mode of aiming light may be appropriately changed. For example, when irradiating only aiming light onto the tissue, the CPU 41 may execute driving control for the laser scanner 30 different from driving control when irradiating treatment laser light. As an example, the CPU 41 may divide a plurality of spots in the arrangement pattern into two or more groups and may sequentially switch a group onto which aiming light is emitted while treatment laser light is not emitted (see JP-A-2011-224345). In this case, the operator can determine a position about to be emitted while confirming the appearance of a tissue onto which treatment laser light is about to be emitted. The CPU 41 may change at least one of color of aiming light, a blinking interval, a scanning speed of aiming light by the laser scanner 30, an irradiation order of aiming light for the respective spots, and the like between a period in which treatment laser light is not emitted and a period in which treatment laser light is emitted. In this case, the operator can recognize whether or not treatment laser light is emitted by the irradiation mode of aiming light. Aiming light may be off during the irradiation of treatment laser light. Aiming light may be in a continuous-wave form, instead of a pulse form.

The CPU 41 may show the operator a region which is treated in the set arrangement pattern without sequentially irradiating aiming light onto the respective spots in the arrangement pattern. For example, aiming light may be scanned along the peripheral portion of the region which is treated in the arrangement pattern. In this case, the operator can determine a position about to be emitted while confirming the appearance of the tissue onto which treatment laser light is about to be emitted.

Figure 3:
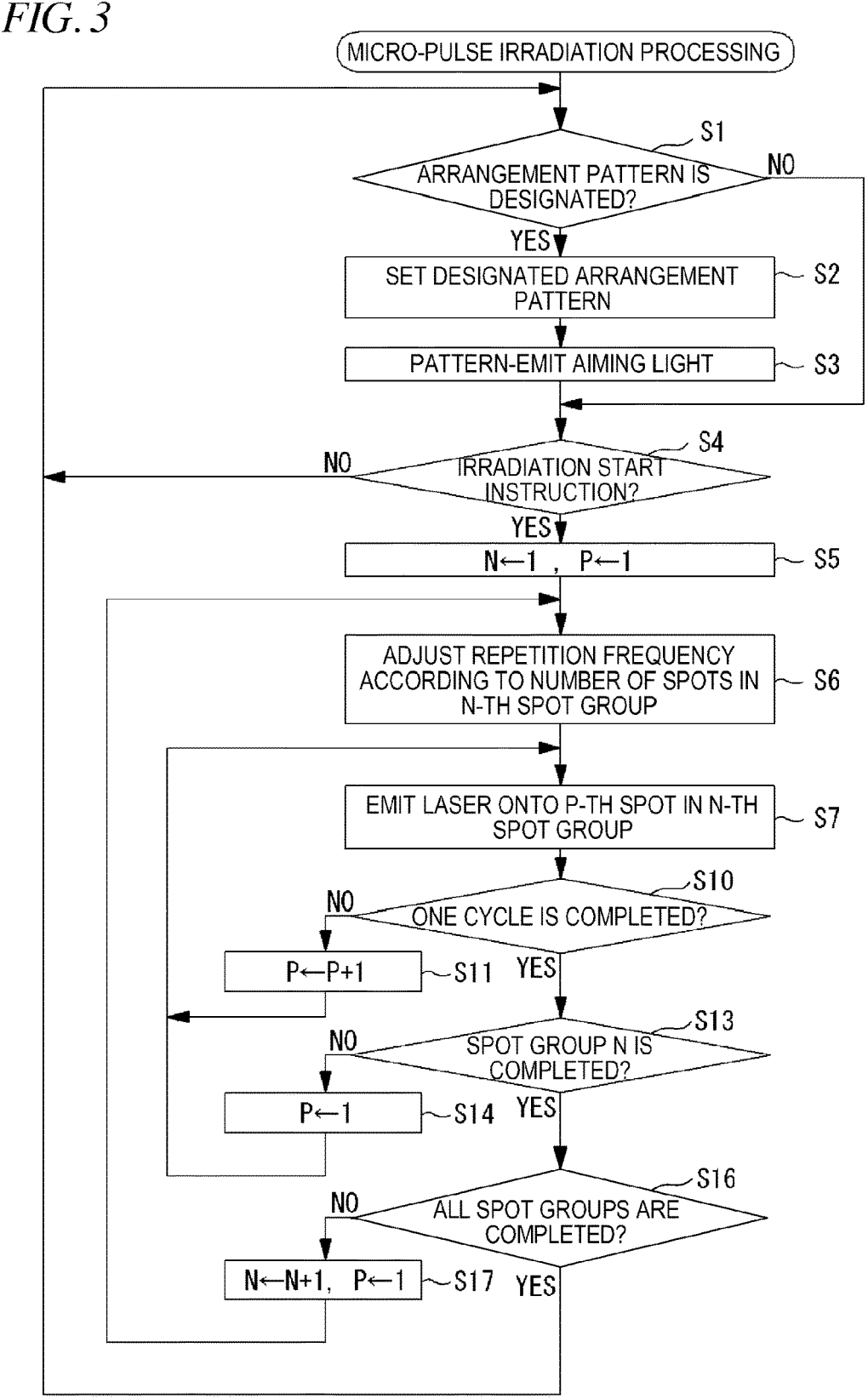
FIG. 3 is a flowchart of micro-pulse irradiation processing which is executed by the laser treatment apparatus 1.

Returning to the description of FIG. 3, if the irradiation start instruction is performed (S4: YES), processing for irradiating treatment laser light according to the set irradiation pattern is performed (S5 to S17). First, the values of a spot group counter N and an irradiation order counter P are initialized to "1" (S5).

A spot group will be described referring to FIG. 4. A spot group has two or more spots onto which treatment laser light is emitted in the same irradiation cycle. That is, treatment laser light is emitted in parallel (in the example of FIG. 4, alternately) onto a plurality of spots belonging to the same spot group in a process where the irradiation cycle is repeated. FIG. 4 is a diagram schematically showing an arrangement pattern (hereinafter, referred to as "linear pattern") in which six treatment spots are arranged linearly. In the example shown in FIG. 4, of the six spots in the linear pattern, a leftmost spot 61A and a third spot 61B from the right are set in a spot group N=1. In the spot group N=1, an irradiation order P of treatment laser light for the leftmost spot 61A is set to "1", and an irradiation order P of treatment laser light for the third spot 61B from the right is set to "2". A second spot 62A from the left is set to a spot group N=2 and an irradiation order P=1. A second spot 62B from the right is set to a spot group N=2 and an irradiation order P=2. A third spot 63A from the left is set to a spot group N=3 and an irradiation order P=1. A rightmost spot 63B is set to a spot group N=3 and an irradiation order P=2. In this case, in this embodiment, treatment laser light is emitted in parallel onto respective two spots belonging to the same spot group in the irradiation order of "1→2→1→2→ . . . ". If the irradiation of treatment laser light for one spot group ends, the process progresses to parallel irradiation of treatment laser light for the next spot group. If the irradiation of treatment laser light for all of the three spot groups ends, the irradiation of treatment laser light is stopped. The details will be described below referring to FIG. 5.

As described above, the spot group counter N for use in micro-pulse setting processing is a counter which is used to specify a spot group in the set arrangement pattern. The irradiation order counter P is a counter which is used to specify the irradiation order of treatment laser light onto the respective spots belonging to the same spot group.

In this embodiment, as illustrated in FIG. 4, one or a plurality of spot groups are set in each arrangement pattern. The spot groups may be set until treatment laser light starts. In this embodiment, the spot groups are set in each arrangement pattern in advance and programmed. When a user operates the operating unit 50 to create a new arrangement pattern, the user may designate a spot group, and the CPU 41 may automatically set spot groups.

In this embodiment, as illustrated in FIG. 4, when a plurality of spots belonging to the same spot group can be separated from each other, the spot groups are set such that a plurality of spots in each spot group are separated from each other as much as possible. That is, the laser treatment apparatus 1 according to the present embodiment separates a plurality of spots belonging to a spot group to be treated at an inter-center distance greater than the inter-center distance between two adjacent spots when repeating the same irradiation cycle to perform treatment of one spot group. In detail, in the example shown in FIG. 4, the inter-center distance between the spot 61A and the spot 61B belonging to the spot group N=1 is greater than the inter-center distance between two adjacent spots (for example, the spot 61A and the spot 62A). Treatment laser light is emitted in parallel onto a plurality of spots belonging to the same spot group. If a plurality of spots onto which treatment laser light is emitted in parallel are close to each other, heat is difficult to diffuse from a plurality of spots to be treated compared to the spots are separated from each other. The laser treatment apparatus 1 according to the present embodiment separates a plurality of spots, onto which treatment laser light is emitted in parallel, from each other, thereby suppressing the occurrence of adverse influence by heat accumulation.

As the number of spots belonging to the same spot group (that is, the number of spots onto treatment laser light is emitted in each irradiation cycle) increases, it is necessary to increase the scanning speed by the laser scanner 30. When increasing the scanning speed by the laser scanner 30, in general, it is necessary to decrease at least one of the rotatable angle of each of the galvanomirrors 31 and 35 and the size of the reflective surface of each of the galvanomirrors 31 and 35. As a result, it becomes difficult to secure the scanning range of treatment laser light on the fundus. Accordingly, it is preferable that the number of spots belonging to the same spot group is equal to or smaller than 6. In this case, the laser treatment apparatus 1 emits treatment laser light in parallel onto a plurality of spots while securing the scanning range of treatment laser light on the fundus, thereby reducing the treatment time. It is preferable that the number of spots belonging to the same spot group is equal to or smaller than 4.

Returning to the description of FIG. 3, if the spot group counter N and the irradiation order counter P are initialized (S5), the repetition frequency (Pulse Repetition Frequency) of the pulse emitted from the laser light source 11 is adjusted according to the number of spots belonging to an N-th (immediately after the initialization of the counters, first) spot group (S6). For example, when the irradiation cycle times is 2000 microseconds, and when the same irradiation cycle is repeated to treat only one spot, the laser light source 11 may emit the pulse once at every 2000 microseconds. In this case, the pulse repetition frequency of the laser light source 11 becomes 500 Hz. However, when treating two spots in parallel, the laser light source 11 should emit the pulse twice in the irradiation cycle of 2000 microseconds. In this case, the pulse repetition frequency of the laser light source 11 becomes 1000 Hz. That is, in S6, "(the number of spots belonging to the spot group N)/(the irradiation cycle time)" is calculated, whereby the pulse repetition frequency of the laser light source 11 is obtained. The laser light source 11 is driven according to the obtained repetition frequency. The laser light source 11 according to the present embodiment sequentially emits a plurality of pulses at a constant interval.

Next, the CPU 41 drives the laser scanner 30, thereby allowing one of the pulses sequentially emitted from the laser light source 11 to be emitted onto a spot having a P-th irradiation order of the N-th spot group (S7). It is determined whether or not one irradiation cycle is completed (that is, whether or not the pulse is emitted onto all spots belonging to the N-th spot group once) (S10). If one irradiation cycle is not completed (S10: NO), the value of the irradiation order counter P is incremented by "1" (S11), and the process returns to S7. In this case, in S7, a pulse next emitted from the laser light source 11 is emitted onto a spot having the next irradiation order. When one spot is treated in one irradiation cycle, the determination of S10 becomes "YES".

If one irradiation cycle is completed (S10: YES), it is determined whether or not the irradiation of the pulse multiple times for the N-th spot group is completed (S13). In this embodiment, it is determined whether or not the irradiation of the pulse for the N-th spot group is completed according to whether or not the elapsed time from the start of treatment for the N-th spot group reaches the intermittent irradiation time. If the irradiation is not completed (S13: NO), the value of the irradiation order counter P is initialized and becomes "1" (S14), and the process returns to S7. As a result, the same irradiation cycle is repeated.

When the irradiation of the pulse for the N-th spot group is completed (S13: YES), it is determined whether or not treatment of all spot groups belonging to the irradiation pattern set in S2 is completed (S16). If treatment is not completed (S16: NO), the value of the spot group counter N is incremented by "1", the irradiation order counter P becomes "1" (S17), and the process returns to S6. Thereafter, processing for irradiating the pulse for the next spot group is performed (S6 to S13). When treatment of all spot groups is completed (S16: YES), the emission of the pulse from the laser light source 11 is stopped, and the process returns to the determination of S1. If an instruction to end treatment by micro-pulse is input, the micro-pulse irradiation processing ends.

Figure 5:
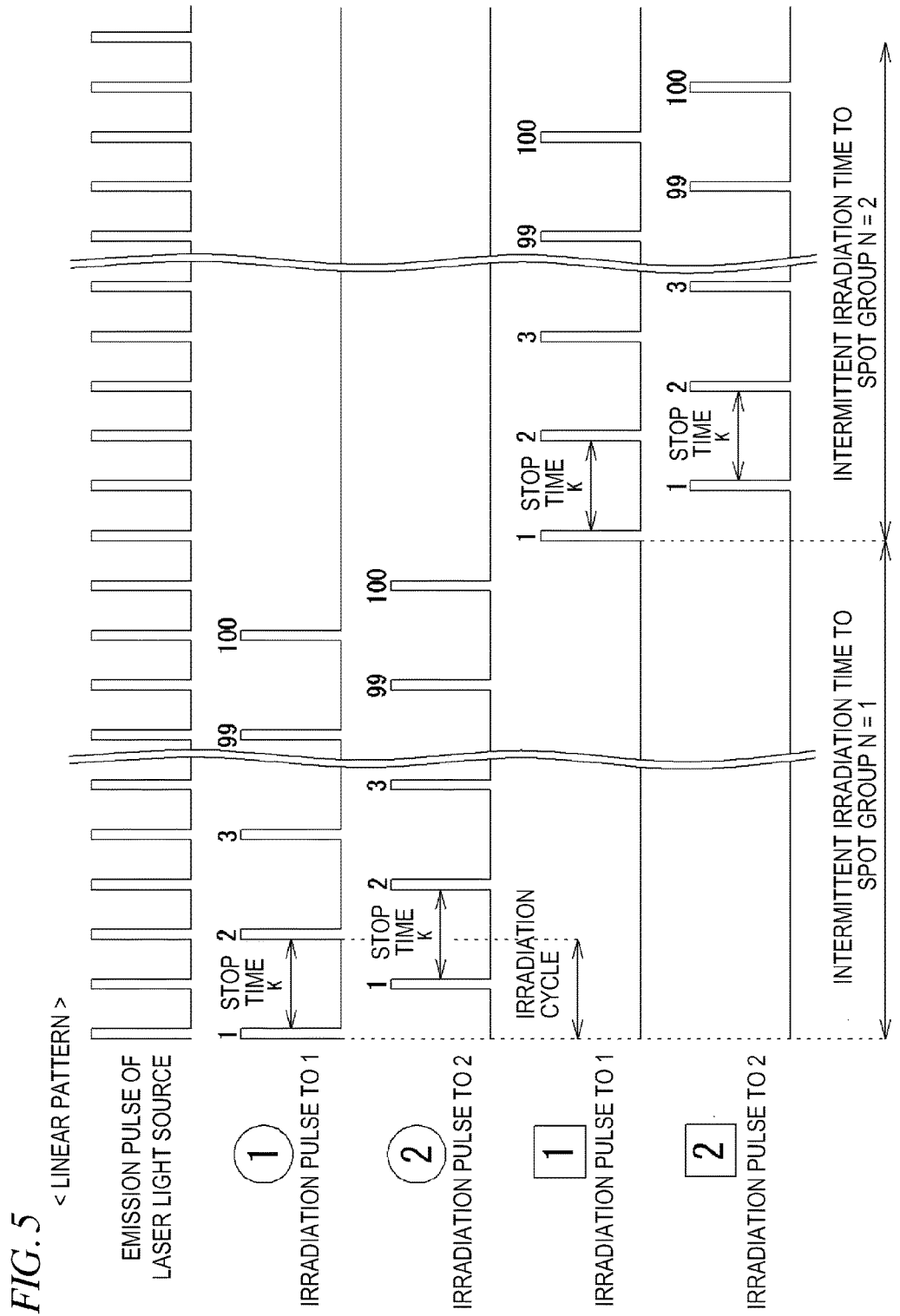
FIG. 5 is a timing chart showing an example of an irradiation mode when irradiating treatment laser light along the linear pattern shown in FIG. 4.

An irradiation mode when irradiating the pulse of treatment laser light along the linear pattern shown in FIG. 4 will be described in detail referring to FIG. 5. In the following example, a case where the pulse width is set to 200 microseconds, the stop time is set to 1800 microseconds, the irradiation cycle time is set to 2000 microseconds, and the intermittent irradiation time is set to 0.2 seconds will be described.

First, in the linear pattern shown in FIG. 4, two spots belong to each of the three spot groups. Accordingly, the pulse repetition frequency of the laser light source 11 is adjusted such that two pulses are emitted while each irradiation cycle is performed. The first pulse emitted from the laser light source 11 is emitted onto a spot having a first irradiation order between the two spots belonging to the first spot group. Next, the second pulse emitted from the laser light source 11 is emitted onto a spot having a second irradiation order between the two spots belonging to the first spot group. Thereafter, one irradiation cycle ends. This irradiation cycle is repeated 100 times until the intermittent irradiation time elapses. As a result, the pulse is emitted onto each of the two spots belonging to the first spot group 100 times at the same time interval (stop time). If the intermittent irradiation of the pulse for the first spot group is completed, the intermittent irradiation of the pulse for the second spot group is executed in the same procedure as the irradiation for the first spot group.

The laser treatment apparatus 1 according to the present embodiment can cause the pulse to be emitted onto the second spot for the stop time in the irradiation cycle from when the irradiation of the pulse for the first spot starts until the pulse is emitted again onto the spot having the first irradiation order after the stop time. Accordingly, it is possible to reduce treatment time compared to a case where no pulse is emitted onto any spot for the stop time. Considering based on the spot having the second irradiation order, the pulse is emitted onto the first spot for the stop time during which the irradiation of the pulse onto the second spot is stopped. Therefore, in this embodiment, the irradiation of the pulse onto a different spot is performed for the stop time in each spot.

Figure 6:
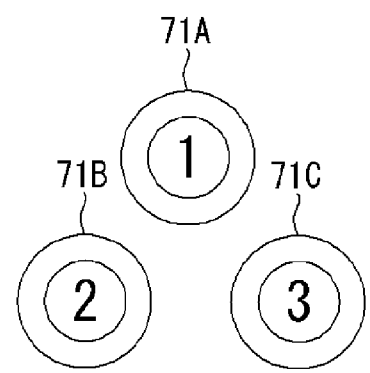
FIG. 6 is a diagram showing an example of the arrangement and spot groups of a triangular pattern.
Figure 7:
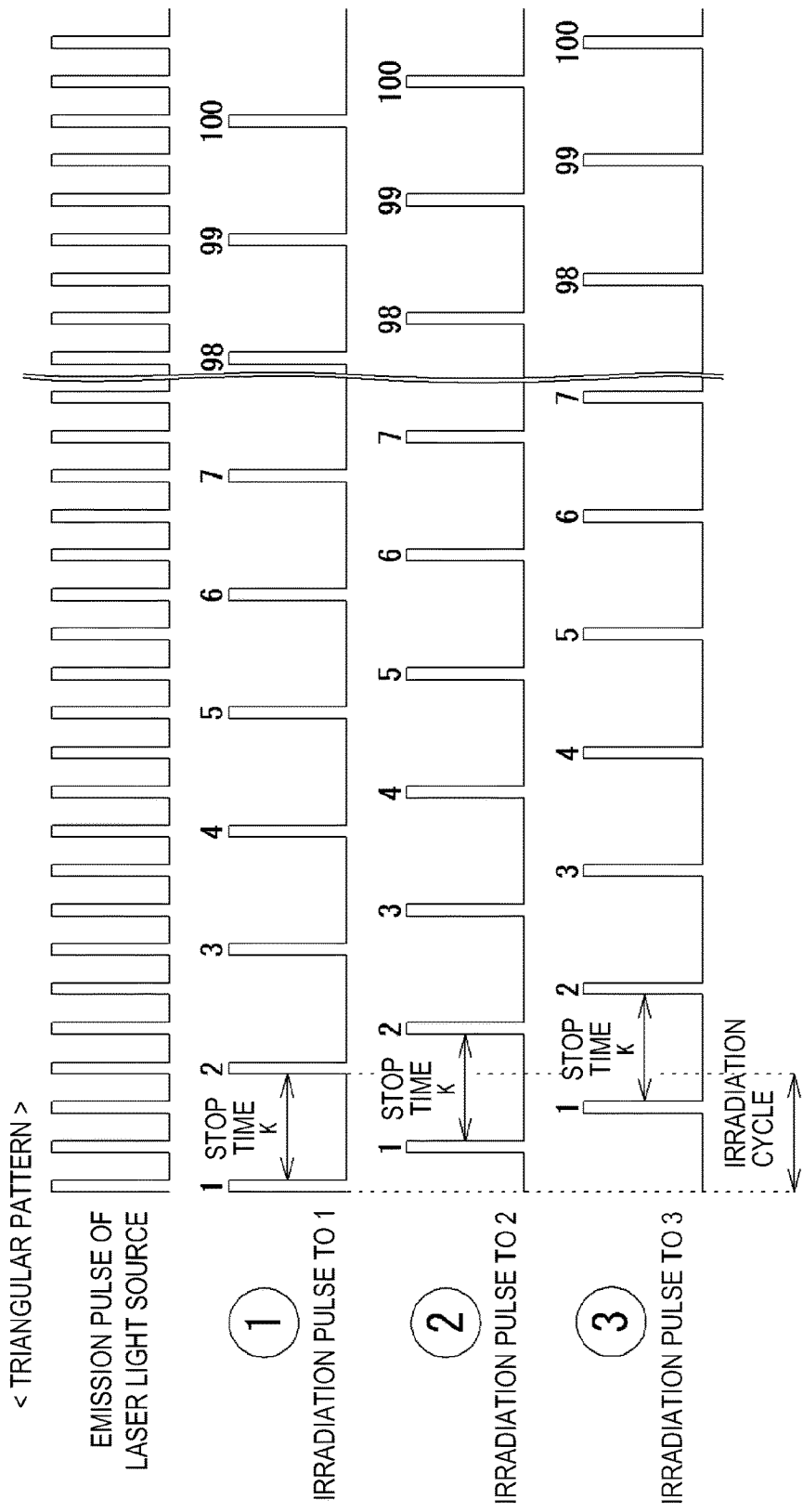
FIG. 7 is a timing chart showing an example of an irradiation mode when irradiating treatment laser light along the triangular pattern shown in FIG. 6.

Referring to FIGS. 6 and 7, an irradiation mode when irradiating the pulse of treatment laser light according to a triangular pattern which is one of a plurality of arrangement patterns will be described. In the triangular pattern illustrated in FIG. 6, three spots 71A, 71B, and 71C are arranged so as to become the apexes of a triangle. In the above-described linear pattern (see FIG. 4), two spots belong to one spot group. In the example shown in FIG. 6, all three spots belong to the same spot group. In this way, the number of spots belonging to one spot group may be appropriately set according to, for example, performance of the laser scanner 30, the length of the stop time, or the like.

As shown in FIG. 7, in the triangular pattern shown in FIG. 6, three spots belong to one spot group. Accordingly, the pulse repetition frequency of the laser light source 11 is adjusted such that three pulses are emitted while each irradiation cycle is performed. The first pulse emitted from the laser light source 11 is emitted onto a spot having a first irradiation order. Next, the second pulse emitted from the laser light source 11 is emitted onto a spot having a second irradiation order. The third pulse emitted from the laser light source 11 is emitted onto a third irradiation order. Thereafter, one irradiation cycle ends. This irradiation cycle is repeated until the intermittent irradiation time elapses. As a result, the pulse is emitted onto each of three spots belonging to one spot group intermittently at the same time interval. In this embodiment, the number of spots belonging to one spot group is set to be equal to or smaller than 3. As a result, the rotatable angle and the size of the reflective surface of each of the galvanomirrors 31 and 35 in the laser scanner 30 are secured.

Figure 8:
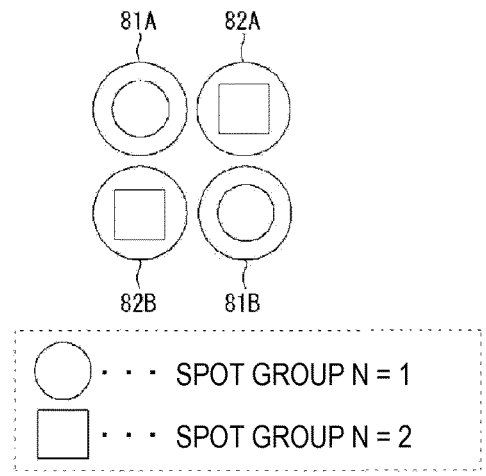
FIG. 8 is a diagram showing an example of the arrangement and spot groups of a 2×2 square pattern.

Referring to FIG. 8, a 2×2 square pattern which is one of a plurality of arrangement patterns will be described. In the 2×2 square pattern illustrated in FIG. 8, four spots 81A, 81B, 82A, and 82B are arranged so as to become the apexes of a square. A spot group N=1 is formed by an upper left spot 81A and a lower right spot 81B. A spot group N=2 is formed by an upper right spot 82A and a lower left spot 82B. In the 2×2 square pattern, the distance between two adjacent spots horizontally and vertically is the shortest distance between two spots. In this embodiment, a spot group is formed by two spots located obliquely (on a diagonal line). As a result, the inter-center distance between two spots belonging to one spot group becomes longer than a case where a spot group is formed by two spots located horizontally or vertically (that is, than the inter-center distance between two adjacent spots). Therefore, heat generated by treatment laser light is easily diffused.

Figure 9:
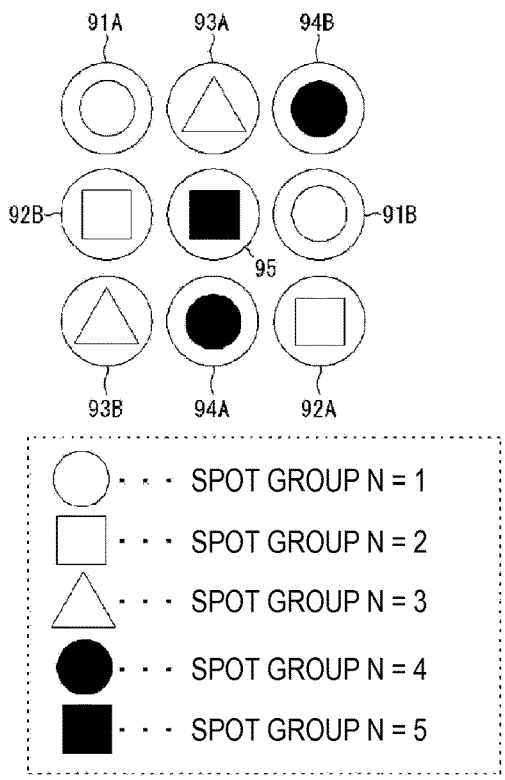
FIG. 9 is a diagram showing an example of the arrangement and spot groups of a 3×3 square pattern.

Referring to FIG. 9, a 3×3 square pattern which is one of a plurality of arrangement pattern will be described. In the 3×3 square pattern illustrated in FIG. 9, 9 spots in total of vertical 3 places×horizontal 3 places are arranged equally in a square shape. In the 3×3 square pattern according to the present embodiment, each of spot groups N=1 to 4 is formed by two spots. That is, an irradiation cycle for treating the spot groups N=1 to 4 is a parallel irradiation cycle for treating a plurality of spots in parallel. A spot group N=5 has one spot. That is, an irradiation cycle for treating the spot group N=5 is a single irradiation cycle. In this way, when sequentially irradiating the pulse onto a plurality of spot groups based on each irradiation start instruction, the number of spots belonging to each of a plurality of spot groups is not necessarily equal. In this case, it is preferable that the repetition frequency of the laser light source 11 is adjusted such that the stop time for each of a plurality of spots becomes equal. The laser treatment apparatus 1 according to the present embodiment emits the pulse onto one spot belonging to the spot group N=5 in a state where the repetition frequency when irradiating the pulse onto the spots of the spot groups N=1 to 4 is changed to half. As a result, the difference in treatment effect between the respective spots is suppressed. When a standby time for changing the repetition frequency of the laser light source 11 is required, the laser treatment apparatus 1 may restart the irradiation of laser light onto the tissue after the standby time has elapsed and the repetition frequency is stabilized.

As described above, when causing treatment laser light to be emitted onto each of a plurality of spots intermittently multiple times, the laser treatment apparatus 1 according to the present embodiment can execute the irradiation of treatment laser light of a different spot for the stop time during which the emitted of treatment laser light for one spot is stopped. In other words, while the CPU 41 according to the present embodiment causes treatment laser light to be emitted onto a first spot and then returns the irradiation position of treatment laser light to the first spot after the set stop time has elapsed, treatment laser light is emitted onto one or a plurality of spots other than the first spot for the stop time. Therefore, in the laser treatment apparatus 1 according to the present embodiment, it is possible to reduce treatment time compared to a case where treatment laser light is not emitted onto any spot for the stop time.

In this embodiment, each pulse of treatment laser light is scanned by the laser scanner 30. In this case, the laser treatment apparatus 1 can appropriately control the irradiation time of treatment laser light emitted onto each spot multiple times by adjusting the pulse width of each pulse. In the treatment of the patient's eye E by micro-pulse, when reducing the influence of heat diffused from a region to be treated, it is necessary to emit the pulse onto each spot intermittently through the stop time. In the related art, it is difficult to attain a technique which emits the pulse for the stop time since an approach opposite to the principle of treatment using micro-pulse should be performed. The inventors according to the present embodiment realize reduction in the time necessary for micro-pulse irradiation treatment while overcoming the above-described difficulty.

In a general intermittent irradiation treatment of the related art, there is a case where an operation to cause treatment laser light to be emitted onto one spot intensively at the same time interval is repeated in order for a plurality of spots. In the laser treatment apparatus 1 according to the present embodiment, the time interval when causing treatment laser light to be emitted onto each spot intermittently is uniform, thereby efficiently obtaining the same treatment effects as the effects obtained by treatment in the related art compared to the related art.

In the intermittent irradiation treatment, there is a case where an effect (hereinafter, referred to as "heat diffusion prevention effect") of permitting heat to be less diffused from a tissue to be treated to surrounding tissues is obtained compared to treatment in which continuous waves (CW) are emitted onto each spot continuously. The laser treatment apparatus 1 according to the present embodiment can separate a plurality of spots, onto which treatment laser light is emitted in parallel, from each other by the repetition of the irradiation cycle. In this case, the laser treatment apparatus 1 can suppress reduction in heat diffusion prevention effect.

The laser treatment apparatus 1 according to the present embodiment sets a spot arrangement pattern. When a plurality of spots are included in the set arrangement pattern, control (parallel irradiation control) is performed such that treatment laser light is emitted onto a plurality of spots in one irradiation cycle. Accordingly, the laser treatment apparatus 1 can efficiently emit treatment laser light according to the set arrangement pattern.

In this embodiment, spot groups onto which treatment laser light is emitted in the same irradiation cycle are set in each arrangement pattern. Parallel irradiation is performed for the spot groups set in the arrangement pattern. Accordingly, the laser treatment apparatus 1 can efficiently emit treatment laser light according to the arrangement pattern.

The laser treatment apparatus 1 according to the present embodiment can scan aiming light in the set arrangement pattern. Accordingly, the operator can easily recognize the arrangement pattern of the spots, onto which treatment laser light is emitted, by aiming light.

The technique disclosed in the above-described embodiment is just an example. Accordingly, the contents disclosed in the above-described embodiment may be changed. The laser treatment apparatus 1 of the embodiment scans the pulse emitted (oscillated) intermittently from the laser light source 11, thereby executing the intermittent irradiation treatment for a plurality of spots in parallel each time the irradiation start instruction of treatment laser light is performed. As a result, the irradiation time of treatment laser light emitted onto each spot is appropriately controlled. However, the technique illustrated in the above-described embodiment can also be applied to a laser treatment apparatus which repeatedly scans continuous waves (CW) emitted intermittently onto the spots to perform the intermittent irradiation treatment. When scanning continuous waves from one spot to a different spot, treatment laser light is emitted between two spots in addition to each of the two spots. However, since the influence of treatment laser light emitted between two spots is reduced by increasing the scanning speed, the same treatment effects as the intermittent irradiation treatment of the related art may be obtained.

In the foregoing embodiment, treatment in which micro-pulse is emitted onto the fundus intermittently has been illustrated. However, the technique illustrated in the above-described embodiment can be applied to other kinds of treatment. For example, when performing selective retina therapy (SRT) in diabetic macular edema (DME), the technique illustrated in the above-described embodiment may be applied. In the SRT, treatment laser light is emitted onto the fundus at a very short pulse width (for example, the pulse width is 1.7 microseconds, the pulse repetition frequency is 100 Hz, and the like). When performing selective laser trabeculoplasty (SLT), the technique illustrated in the above-described embodiment may be applied.

When continuously executing multiple irradiation cycles, the laser treatment apparatus 1 according to the present embodiment makes the time of each irradiation cycle constant. The laser treatment apparatus 1 makes the irradiation order, the irradiation timing, and the number of irradiations of treatment laser light for a plurality of spots equal in multiple parallel irradiation cycles. As a result, the irradiation interval (stop time) treatment laser light is made constant. However, multiple parallel irradiation cycles may be executed while changing at least one of the pulse width, the stop time, the irradiation cycle time, the irradiation order, and the number of irradiations. In this case, the time necessary for treatment is shortened compared to the related art. As an example, energy which is stronger than energy to be applied to other spots is applied to some of a plurality of spots in an arrangement pattern (for example, spots at four corners of a rectangular arrangement pattern), and a treatment trace is left in some spots. If a treatment race is left in some spots, the operator can understand a treated region from the left treatment trace. In this case, the laser treatment apparatus 1 may change energy to be applied to the spots among the spots by changing at least one of the pulse width, the stop time, the irradiation cycle time, the irradiation order, and the number of irradiations. In the above-described embodiment, intermittent irradiation of treatment laser light for the same spot group is executed by repeating the same irradiation cycle. However, treatment laser light may be emitted onto a plurality of spots belonging to one spot group by repeating different irradiation cycles.

The laser treatment apparatus 1 according to the present embodiment scans the pulses emitted intermittently at a constant time interval to sequentially emit the pulses onto a plurality of spots. Accordingly, the control of the laser scanner 30 is facilitated compared to a case where the interval of the pulses emitted from the laser light source 11 is not constant. However, even if the laser light source 11 does not oscillate the pulse at a constant interval, it is possible to realize the technique illustrated in the above-described embodiment.

The laser treatment apparatus 1 according to the present embodiment can separate a plurality of spots, onto which treatment laser light is intermittently emitted in parallel, from each other. As a result, the heat diffusion prevention effect is unlikely to be reduced. However, the laser treatment apparatus 1 does not need to separate a plurality of spots, onto which treatment laser light is emitted in parallel, from each other in all cases.

What is claimed is:

1. A laser treatment apparatus configured to emit laser light onto a tissue of a patient's eye, the laser treatment apparatus comprising:
    a laser light source;
    a laser scanner configured to scan laser light emitted from the laser light source and switch a position of the tissue onto which laser light is emitted;
    a processor; and
    memory storing computer readable instructions comprises a first mode, which when executed by the processor, causes the laser treatment apparatus to:
    (a) emit the laser light onto a first spot;
    (b) stop emitting the laser light onto the first spot for a stop time;
    (c) emit the laser light onto a second spot during the stop time;
    (d) emit the laser light onto the first spot again after the stop time elapses; and
    repeat (b), (c) and (d) a plurality of times to execute intermittent irradiation treatment onto the first spot and the second spot multiple times;
    wherein the emitted laser light is a treatment laser light; and
    wherein the computer readable instructions further comprises a second mode, which when executed by the processor, causes the laser treatment apparatus to execute a single irradiation treatment in which laser light has energy higher than laser light emitted onto the tissue during the first mode and in which the intermittent irradiation treatment is emitted onto each spot once; and
    wherein the laser light emitted during the intermittent irradiation treatment in the first mode and the laser light emitted during the single irradiation treatment in the second mode are emitted from the same laser light source and scanned by the same laser scanner configured to output at both a high energy and a low energy.

2. The laser treatment apparatus according to claim 1, wherein
    the computer readable instructions when executed identify a third spot; and wherein
    a distance between the first spot to the second spot is greater than a distance between the first spot and the third spot.

3. The laser treatment apparatus according to claim 1, wherein, in each irradiation cycle defined by a period between (a) and (d), the number of spots onto which laser light is emitted is equal to or less than 6.

4. The laser treatment apparatus according to claim 1, wherein, in each irradiation cycle defined by a period between (a) and (d), the number of spots onto which laser light is emitted is equal to or less than 3.

5. The laser treatment apparatus according to claim 1 further comprising:
    a pattern setter configured to set an arrangement pattern defining an arrangement of each of the treatment spots onto which laser light is emitted,
    wherein, when the treatment spots are included in the arrangement pattern set by the pattern setter, the computer readable instructions when executed by the processor causes the laser treatment apparatus to execute parallel irradiation control for causing laser light to be emitted onto two or more of the treatment spots in one irradiation cycle defined by a period between (a) and (d).

6. The laser treatment apparatus according to claim 5, wherein
    at least one spot group having two or more of the treatment spots, onto which laser light is emitted in the same irradiation cycle, are set in each arrangement pattern, and
    when the treatment spots are included in the arrangement pattern set by the pattern setter, the computer readable instructions when executed by the processor causes the laser treatment apparatus to execute the parallel irradiation control for each spot group set in the arrangement pattern.

7. The laser treatment apparatus according to claim 5, further comprising:
    an aiming light source configured to emit aiming light indicating a position of the treatment spot, wherein the computer readable instructions when executed by the processor causes the laser treatment apparatus to:
control operation of the laser scanner to cause the aiming light to be emitted onto the tissue in an arrangement pattern set by the pattern setter.

8. The laser treatment apparatus according to claim 1, wherein
when the intermittent irradiation treatment is executed, laser light emitted from the laser light source is emitted onto the tissue in a pulsed manner by alternately repeating on and off the laser light source, and the laser scanner scans the pulse of laser light emitted onto the tissue.

9. The laser treatment apparatus according to claim 8, wherein
the computer readable instructions when executed by the processor causes the laser treatment apparatus to emit the pulse of laser light onto at least one spot at a constant time interval multiple times when the intermittent irradiation treatment is executed.

10. The laser treatment apparatus according to claim 8, wherein the computer readable instructions when executed by the processor causes the laser treatment apparatus to adjust a repetition frequency of a pulse emitted from the laser light source according to the number of spots onto which laser light is emitted in each irradiation cycle defined by a period between (a) and (d).

11. The laser treatment apparatus according to claim 8, wherein
the computer readable instructions when executed by the processor causes the laser treatment apparatus to carry out the following additional steps following steps (d):
(e) emit the laser light onto a third spot,
(f) stop emitting the laser light onto the third spot for a stop time,
(g) emit the laser light onto a fourth spot during the stop time;
(h) emit the laser light onto the third spot again after the stop time elapses; and
(i) repeat (f), (g) and (h) a plurality of times to execute intermittent irradiation treatment onto the third and fourth spots multiple times.

12. The laser treatment apparatus according to claim 11, wherein
the first spot is adjacent to the third spot,
a distance between the first spot and the second spot is set greater than a distance between the first spot and the third spot.

13. The laser treatment apparatus according to claim 11, wherein
a plurality of spots which includes the first, second, third and fourth spots are arranged,
the first spot is not disposed adjacent to the second spot, the third spot is not disposed adjacent to the fourth spot.

14. The laser treatment apparatus according to claim 1, wherein the laser scanner includes at least one galvanomirror configured to scan the laser light by rotating the galvanomirrors around an oscillation axis.

15. The laser treatment apparatus according to claim 14, wherein at least one of the galvanomirrors is rotatable at equal to or greater than 1.5 degrees based on an origin position.

16. The laser treatment apparatus according to claim 15, wherein a reflection surface of at least one of the galvanomirrors has a size equal to or greater than 8 mm in an axial direction of the oscillation axis.

17. A method of controlling the laser treatment apparatus according to claim 1, comprising:
(a) emitting the laser light onto the first spot;
(b) stopping emitting the laser light onto the first spot for the stop time;
(c) emitting the laser light onto the second spot during the stop time;
(d) emitting the laser light onto the first spot again after the stop time elapses; and
repeating (b), (c) and (d) several times to execute intermittent irradiation treatment onto plurality of spots multiple times.

* * * * *